US00PP12572P2

(12) United States Plant Patent

Bartels

(10) Patent No.: US PP12,572 P2

(45) Date of Patent: Apr. 23, 2002

(54) PHLOX PLANT NAMED 'BARFIVE'

(75) Inventor: Gosen B. H. Bartels, Aalsmeer (NL)

(73) Assignee: Bartels Breeding B.V., Aalsmeer (NL)

( * ) Notice: Subject to any disclaimer, the term of this patent is extended or adjusted under 35 U.S.C. 154(b) by 0 days.

(21) Appl. No.: 09/328,638

(22) Filed: Jun. 9, 1999

(51) Int. Cl.[7] ..... A01H 5/00

(52) U.S. Cl. ..... Plt./320

(58) Field of Search ..... Plt./320

(56) References Cited

PUBLICATIONS

UPOV ROM GTITM Computer Database 2000/04, GTI JOUVERetrieval Software, citation for 'Barfive', Aug. 2000.*

* cited by examiner

*Primary Examiner*—Bruce R. Campell
*Assistant Examiner*—Wendy C Baker
(74) *Attorney, Agent, or Firm*—C. A. Whealy

(57) ABSTRACT

A distinct cultivar of Phlox plant named 'Barfive', characterized by its upright plant habit; relatively fast growth rate; dark green foliage color; attractive pure white flowers with reddish purple throat; and excellent postproduction longevity.

1 Drawing Sheet

BACKGROUND OF THE INVENTION

The present invention relates to a new and distinct cultivar of Phlox plant, botanically known as *Phlox paniculata,* and hereinafter referred to by the cultivar name Barfive.

The new Phlox is a product of a planned breeding program conducted by the Inventor in Aalsmeer, The Netherlands. The objective of the breeding program was to create new Phlox cultivars having desirable cut flower characteristics.

The new Phlox originated from a cross made by the Inventor of two proprietary Phlox seedling selections identified as code number 90.44.07.01 as the female, or seed, parent and PV 03 as the male, or pollen, parent. The cultivar Barfive was discovered and selected by the Inventor as a flowering plant within the progeny of the stated cross in a controlled environment in Aalsmeer, The Netherlands, in 1994.

Plants of the new Phlox differ from plants of the female parent primarily in flower color as plants of the female parent have pink-colored flowers. In addition, plants of the new Phlox have longer postproduction longevity than plants of the female parent. Plants of the new Phlox differ from plants of the male parent primarily in flower color as plants of the male parent have red-colored flowers. In addition, plants of the new Phlox have smaller leaves, smaller flowers and more rounded panicles than plants of the male parent.

Asexual reproduction of the new cultivar by terminal cuttings taken at Aalsmeer, The Netherlands, has shown that the unique features of this new Phlox are stable and reproduced true to type in successive generations.

SUMMARY OF THE INVENTION

Plants of the cultivar Barfive have not been observed under all possible environmental conditions. The phenotype may vary somewhat with variations in environment such as temperature, light intensity, daylength, and fertility level without, however, any variance in genotype.

The following traits have been repeatedly observed and are determined to be the unique characteristics of 'Barfive'. These characteristics in combination distinguish 'Barfive' as a new and distinct cultivar:

1. Upright plant habit.
2. Relatively fast growth rate.
3. Dark green foliage color.
4. Attractive pure white flowers with reddish purple throat.
5. Excellent postproduction longevity.

BRIEF DESCRIPTION OF THE PHOTOGRAPH

The accompanying colored photograph illustrates the overall appearance of the new cultivar, showing the colors as true as it is reasonably possible to obtain in colored reproductions of this type. The photograph comprises a close-up view of typical flowers of the new Phlox. Flower colors in the photograph may appear different than the actual colors due to light reflectance.

DETAILED BOTANICAL DESCRIPTION

In the following description, color references are made to The Royal Horticultural Society Colour Chart except where general terms of ordinary dictionary significance are used.

Plants used for the description were grown under outdoor production conditions with average day and night temperatures of about 16 and 14° C., respectively, in Aalsmeer, The Netherlands.

Botanical classification: *Phlox paniculata* cultivar Barfive.

Parentage:

*Female parent.*—Proprietary *Phlox paniculata* selection identified as 90.44.07.01, not patented.

*Male parent.*—Proprietary *Phlox paniculata* selection identified as PV 03, not patented.

Propagation:

*Type.*—By cuttings.

*Time to initiate roots.*—Summer: About 21 days at 18° C. Winter: About 35 days at 18° C.

*Time to develop roots* (*time to produce a rooted liner*) .—Summer: About 28 days at 18° C. Winter: About 42 days at 18° C.

*Root description.*—Thick in diameter.

Plant description:

*Crop time.*—From cuttings, about 12 weeks are required to produce a flowering plant with harvestable cut flowers.

*Form.*—Strong, upright and tall perennial herb. Typically grown for cut flower production.

*Plant height.*—About 90 cm.

*Plant width.*—About 25 cm.

*Vigor.*—Moderate.

*Lateral branches.*—Quantity: Pinching enhances lateral branch development; typically four per plant. Diameter: About 3 mm. Internode length: About 5 cm. Fasciation: Not observed. Texture: Glabrous. Color: 137A.

*Foliage description.*—Leaves simple, generally symmetrical, and long persisting. Tolerant to stresses. Quantity per lateral branch: Typically about 30. Arrangement: Alternate. Length: About 8 cm. Width: About 4 cm. Shape: Oblong/elliptic. Apex: Sharply acute. Base: Rounded. Margin: Entire. Texture: Leathery. Color: Young foliage, upper surface: 147A. Young foliage, lower surface: 137A. Mature foliage, upper surface: 147A. Mature foliage, lower surface: 137A. Venation, upper surface: 137A. Venation, lower surface: 137A.

Flower description:

*Flower type and habit.*—Single round flowers arranged in terminal panicles; flowers face upright. Panicles globular or pyramidal in shape. Freely flowering. Corolla, salverform, 5-lobed; calyx five-cleft. Flowers last about four days on the plant. Not persistent.

*Natural flowering season.*—Continuously flowering from mid-summer through fall in the Netherlands.

*Quantity.*—Very freely flowering with about 110 flowers per panicle.

*Fragrance.*—Present; typical of species.

*Flower buds.*—Length: About 1 cm. Diameter: About 5 mm. Shape: Elliptic. Rate of opening: About one day.

*Flowers size.*—About 2 cm.

*Petals.*—Quantity: Five, fused. Length: About 2.5 cm. Width: About 1 cm. Shape: Broadly ovate. Apex: Rounded. Margin: Entire. Surface: Typically flat. Texture: Smooth. Color: Upper and lower surfaces, when opening and fully opened: Pure white, 155D; no fading. Base of petals, flower throat (inside) and flower tube (outside), fully opened: Reddish purple, 74A.

*Calyx.*—Shape: Campanulate; sepals, linear, fused at base. Sepal quantity: Five. Sepal apex: Acuminate. Sepal margin: Entire. Texture: Smooth. Color, upper and lower surfaces: 144A.

*Pedicel.*—Strength: Strong. Angle: About 45° to peduncle. Length: About 1 cm. Color: 145A.

*Reproductive organs.*—Pollen: Scarce. Pollen color: 2D. Pistil length: About 2.5 cm. Stigma shape: Three-parted. Stigma color: 154D. Style length: About 2.5 cm. Style color: 154D. Ovary color: 144A.

*Seed development.*—Seed development has not been observed.

Disease resistance: Under commercial conditions, resistance to Powdery Mildew has been observed.

It is claimed:

1. A new and distinct cultivar of Phlox plant named 'Barfive', as illustrated and described.

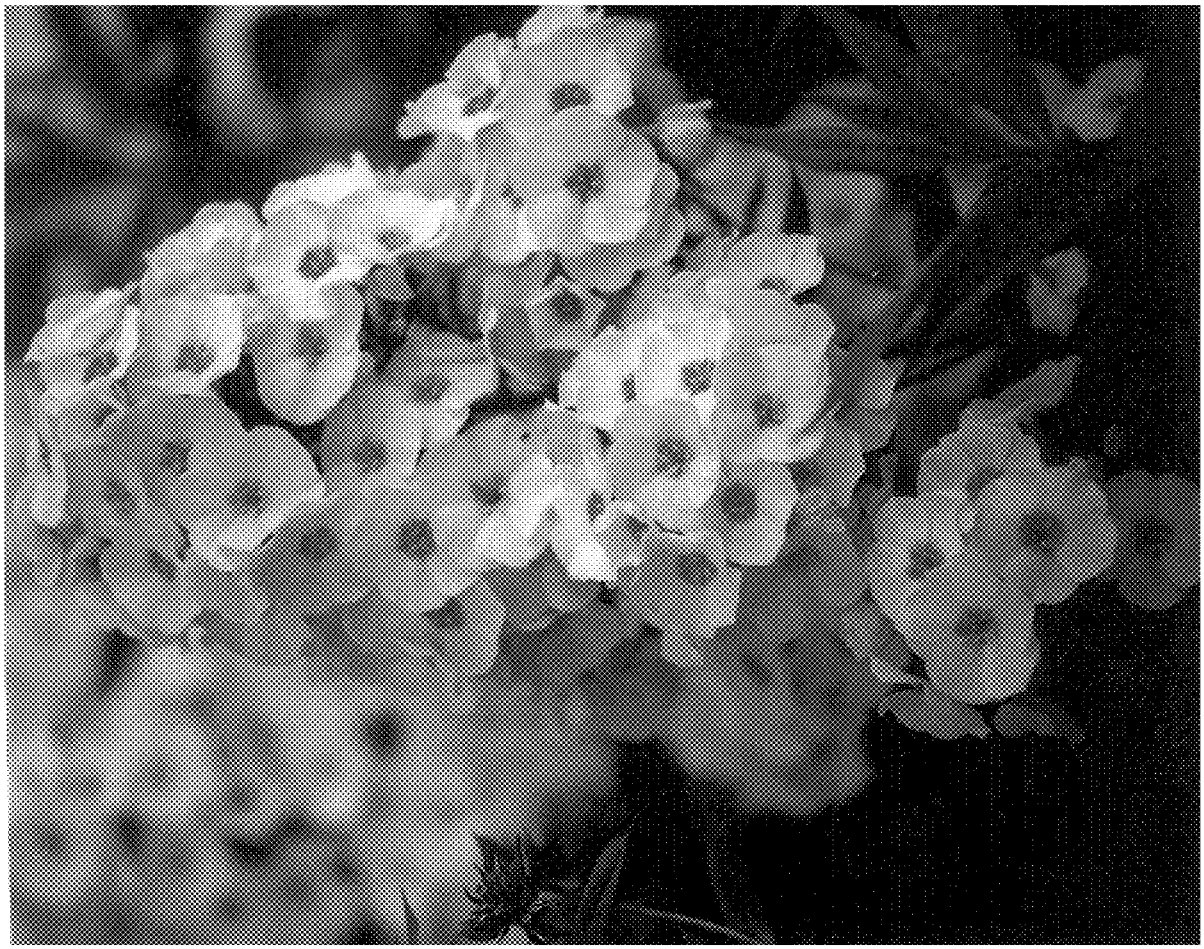

* * * * *